(12) United States Patent
Mamaghani et al.

(10) Patent No.: US 9,028,778 B2
(45) Date of Patent: May 12, 2015

(54) ACCELERATED WRIGHT-GIEMSA AND MAY-GRÜNWALD STAINING METHODS

(71) Applicant: Abbott Laboratories, Abbott Park, IL (US)

(72) Inventors: Abe S. Mamaghani, San Jose, CA (US); Koshy T. Chacko, San Jose, CA (US); Rupa Rao, Santa Clara, CA (US); Rene Nieves, Santa Clara, CA (US)

(73) Assignee: Abbott Laboratories, Abbott Park, IL (US)

( * ) Notice: Subject to any disclaimer, the term of this patent is extended or adjusted under 35 U.S.C. 154(b) by 158 days.

(21) Appl. No.: 13/725,772

(22) Filed: Dec. 21, 2012

(65) Prior Publication Data

US 2013/0177974 A1     Jul. 11, 2013

Related U.S. Application Data

(60) Provisional application No. 61/581,040, filed on Dec. 28, 2011, provisional application No. 61/581,042, filed on Dec. 28, 2011.

(51) Int. Cl.
*A61B 10/00* (2006.01)
*G01N 1/31* (2006.01)
*G01N 1/30* (2006.01)

(52) U.S. Cl.
CPC . *G01N 1/312* (2013.01); *G01N 1/30* (2013.01)

(58) Field of Classification Search
CPC .................................. G01N 1/30; G01N 11/36
USPC ................................. 422/536, 63–67; 436/180
See application file for complete search history.

(56) References Cited

U.S. PATENT DOCUMENTS

| | | | |
|---|---|---|---|
| 5,318,795 A | 6/1994 | Stokes et al. | |
| 5,804,448 A | 9/1998 | Wang et al. | |
| 6,858,432 B2* | 2/2005 | Stokes et al. | 436/46 |
| 7,303,920 B2 | 12/2007 | Stokes et al. | |
| 7,468,161 B2 | 12/2008 | Reinhardt et al. | |
| 7,790,107 B2 | 9/2010 | Nakaya | |
| 2007/0128073 A1 | 6/2007 | Tappen | |

OTHER PUBLICATIONS

Dunning & Safo (2011) "The ultimate Wright-Giemsa stain: 60 years in the making" Biotech Histochem 86(2):69-75.
Teerasaksilp et al. (2005) "Comparative study of blood cell staining with wright-giemsa stain, field stain, and a new modified stain" Lab Hematol 11(1):76-78.
Wittekind et al. (1982) "Azure B-eosin Y stain as the standard Romanowsky-Giemsa stain" Br J Haematol 51 (3):391-393.
Woronzoff-Dashkoff (2002) "The Wright-Giesma Stain: Secrets Revealed" Clin Lab Med 22(1):15-23.

* cited by examiner

*Primary Examiner* — Jyoti Nagpaul
(74) *Attorney, Agent, or Firm* — Edward J. Baba; Benjamin C. Pelletier; Bozicevic, Field & Francis LLP

(57) ABSTRACT

The present disclosure provides methods for carrying out Romanowsky-type stains, specifically Wright-Giemsa and May-Grünwald stains, quickly and efficiently. The methods greatly reduce the overall amount of time required to complete a Wright-Giemsa stain or a May-Grünwald stain of sufficient quality on a biological sample. The subject methods can be applied to both manual and automated staining procedures.

60 Claims, 8 Drawing Sheets

A:

B:

ACCELERATED WRIGHT-GIEMSA AND MAY-GRÜNWALD STAINING METHODS

CROSS REFERENCE TO RELATED APPLICATIONS

Under 35 U.S.C. §119(e), this application claims priority to the filing date of U.S. Provisional Patent Application Ser. No. 61/581,040, filed on Dec. 28, 2011, the disclosure of which application is herein incorporated by reference in its entirety, and to U.S. Provisional Patent Application Ser. No. 61/581,042, filed on Dec. 28, 2011, the disclosure of which application is herein incorporated by reference in its entirety.

BACKGROUND

In the field of tissue staining, there is a type of stain generally referred to as a Romanowsky stain. Romanowsky is generally credited with the discovery of the unique staining effects of thiazin and eosin dyes on blood in 1891. D. Romanowsky (1891) Zur Frage der Parisitologie und Therapie der Malaria, *St Petersb. Med. Wschr.* 16, 297-302, and D. Romanowsky (1891) Zur Frage der Parisitologie und Therapie der Malaria, *St Petersb. Med. Wschr* 16, 307-15. Since that time, many variations of Romanowsky staining have been proposed and created. See, e.g., P. N. Marshall, Romanowsky-Type Stains in Hematology, *Histochem. J.* 10, 1-29 (1978). Modern methods also include those developed by James Wright in the U.S. and Gustav Giemsa in Europe. Combination stains, known as the Wright-Giemsa and May-Grünwald-Giemsa (Pappenheim) stains, are also now widely used, and generally employ mixtures of thiazin and eosin dyes.

The present disclosure provides methods for carrying out Romanowsky-type stains, specifically Wright-Giemsa stains and May-Grünwald stains, quickly and efficiently. The methods provided herein greatly reduce the overall amount of time required to complete a Wright-Giemsa stain or a May-Grünwald stain of sufficient quality on a biological sample. The subject methods can be applied to manual as well as automated staining procedures.

SUMMARY

The present disclosure provides methods for carrying out Romanowsky-type stains, specifically Wright-Giemsa stains and May-Grünwald stains, quickly and efficiently. The methods provided herein greatly reduce the overall amount of time required to complete a Wright-Giemsa stain or a May-Grünwald stain of sufficient quality on a biological sample. The subject methods can be applied to manual as well as automated staining procedures.

In some embodiments, the present disclosure provides an automated staining system for performing a Wright-Giemsa stain on one or more samples, the system including a sample application subsystem that applies a sample to a substrate; a fixation reagent bath; a Wright-Giemsa staining reagent bath; a rinse reagent bath; a sample transfer subsystem for moving the substrate from the sample application subsystem, to the fixation reagent bath, to the Wright-Giemsa staining bath, and then to the rinse reagent bath; and a computer readable storage medium comprising instructions executable by at least one processing device that, when executed, cause the processing device to control the sample transfer subsystem such that the sample transfer subsystem places the one or more samples in the fixation reagent bath for a period of time ranging from about 15 seconds up to about 45 seconds, in the Wright-Giemsa staining reagent bath for a period of time ranging from about 15 seconds up to about 60 seconds, and in the rinse reagent bath for a period of time ranging from about 105 seconds up to about 135 seconds.

In some embodiments, the sample is placed in the fixation reagent bath for a period of time ranging from about 20 seconds up to about 40 seconds. In some embodiments, the sample is placed in the fixation reagent bath for a period of time ranging from about 25 seconds up to about 35 seconds. In some embodiments, the fixation reagent is methanol.

In some embodiments, the sample is placed in the Wright-Giemsa staining reagent bath for a period of time ranging from about 20 seconds up to about 50 seconds. In some embodiments, the sample is placed in the Wright-Giemsa staining reagent bath for a period of time ranging from about 25 seconds up to about 45 seconds. In some embodiments, the Wright-Giemsa staining reagent comprises methanol.

In some embodiments, the sample is placed in the rinse reagent bath for a period of time ranging from about 110 seconds up to about 130 seconds. In some embodiments, the sample is placed in the rinse reagent bath for a period of time ranging from about 115 seconds up to about 125 seconds. In some embodiments, the rinse reagent comprises de-ionized water. In some embodiments, the rinse reagent is a phosphate buffer. In some embodiments, the phosphate buffer is a high salt phosphate buffer. In some embodiments, the phosphate buffer is a low salt phosphate buffer. In some embodiments, the phosphate buffer has a pH value ranging from about 5.0 up to about 9.0 pH units. In some embodiments, the phosphate buffer has a pH value ranging from about 6.5 up to about 7.0 pH units.

In some embodiments, the sample is placed in a second rinse reagent bath for a period of time ranging from about 5 seconds up to about 30 seconds. In some embodiments, the sample is placed in the second rinse reagent bath for a period of time ranging from about 10 seconds up to about 25 seconds. In some embodiments, the sample is placed in the second rinse reagent bath for a period of time ranging from about 10 seconds up to about 20 seconds. In some embodiments, the second rinse reagent comprises de-ionized water. In some embodiments, the second rinse reagent is a phosphate buffer. In some embodiments, the phosphate buffer is a high salt phosphate buffer. In some embodiments, the phosphate buffer is a low salt phosphate buffer. In some embodiments, the phosphate buffer has a pH value ranging from about 5.0 up to about 9.0 pH units. In some embodiments, the phosphate buffer has a pH value ranging from about 6.5 up to about 7.0 pH units. In some embodiments, the sample is placed in a drying chamber.

In some embodiments, the substrate is a glass microscope slide. In some embodiments, the sample is a biological fluid. In some embodiments, the sample is a blood sample. In some embodiments, the sample is a bone marrow sample.

In some embodiments, the present disclosure provides an automated staining system for performing a May-Grünwald stain on one or more samples, the system including a sample application subsystem that applies a sample to a substrate; a fixation reagent bath; a May-Grünwald staining reagent bath; a rinse reagent bath; a sample transfer subsystem for moving the substrate from the sample application subsystem, to the fixation reagent bath, to the May-Grünwald staining bath, and then to the rinse reagent bath; and a computer readable storage medium comprising instructions executable by at least one processing device that, when executed, cause the processing device to control the sample transfer subsystem such that the sample transfer subsystem places the one or more samples in the fixation reagent bath for a period of time ranging from about 15 seconds up to about 45 seconds, in the May-Grünwald staining reagent bath for a period of time ranging from about 165 seconds up to about 195 seconds, and in the rinse reagent bath for a period of time ranging from about 135 seconds up to about 165 seconds.

In some embodiments, the sample is placed in the fixation reagent bath for a period of time ranging from about 20 seconds up to about 40 seconds. In some embodiments, the sample is placed in the fixation reagent bath for a period of time ranging from about 25 seconds up to about 35 seconds. In some embodiments, the fixation reagent is methanol.

In some embodiments, the sample is placed in the May-Grünwald staining reagent bath for a period of time ranging from about 170 seconds up to about 190 seconds. In some embodiments, the sample is placed in the May-Grünwald staining reagent bath for a period of time ranging from about 175 seconds up to about 185 seconds. In some embodiments, the May-Grünwald staining reagent comprises methanol.

In some embodiments, the sample is placed in the rinse reagent bath for a period of time ranging from about 140 seconds up to about 160 seconds. In some embodiments, the sample is placed in the rinse reagent bath for a period of time ranging from about 145 seconds up to about 155 seconds. In some embodiments, the rinse reagent comprises de-ionized water. In some embodiments, the rinse reagent is a phosphate buffer. In some embodiments, the phosphate buffer is a high salt phosphate buffer. In some embodiments, the phosphate buffer is a low salt phosphate buffer. In some embodiments, the phosphate buffer has a pH value ranging from about 5.0 up to about 9.0 pH units. In some embodiments, the phosphate buffer has a pH value ranging from about 6.5 up to about 7.0 pH units.

In some embodiments, the sample is placed in a second rinse reagent bath for a period of time ranging from about 15 seconds up to about 45 seconds. In some embodiments, the sample is placed in the second rinse reagent bath for a period of time ranging from about 20 seconds up to about 40 seconds. In some embodiments, the sample is placed in the second rinse reagent bath for a period of time ranging from about 25 seconds up to about 35 seconds. In some embodiments, the second rinse reagent comprises de-ionized water. In some embodiments, the second rinse reagent is a phosphate buffer. In some embodiments, the phosphate buffer is a high salt phosphate buffer. In some embodiments, the phosphate buffer is a low salt phosphate buffer. In some embodiments, the phosphate buffer has a pH value ranging from about 5.0 up to about 9.0 pH units. In some embodiments, the phosphate buffer has a pH value ranging from about 6.5 up to about 7.0 pH units.

In some embodiments, the substrate is a glass microscope slide. In some embodiments, the sample is a biological fluid. In some embodiments, the sample is a blood sample. In some embodiments, the sample is a bone marrow sample.

DETAILED DESCRIPTION

Figure 1:
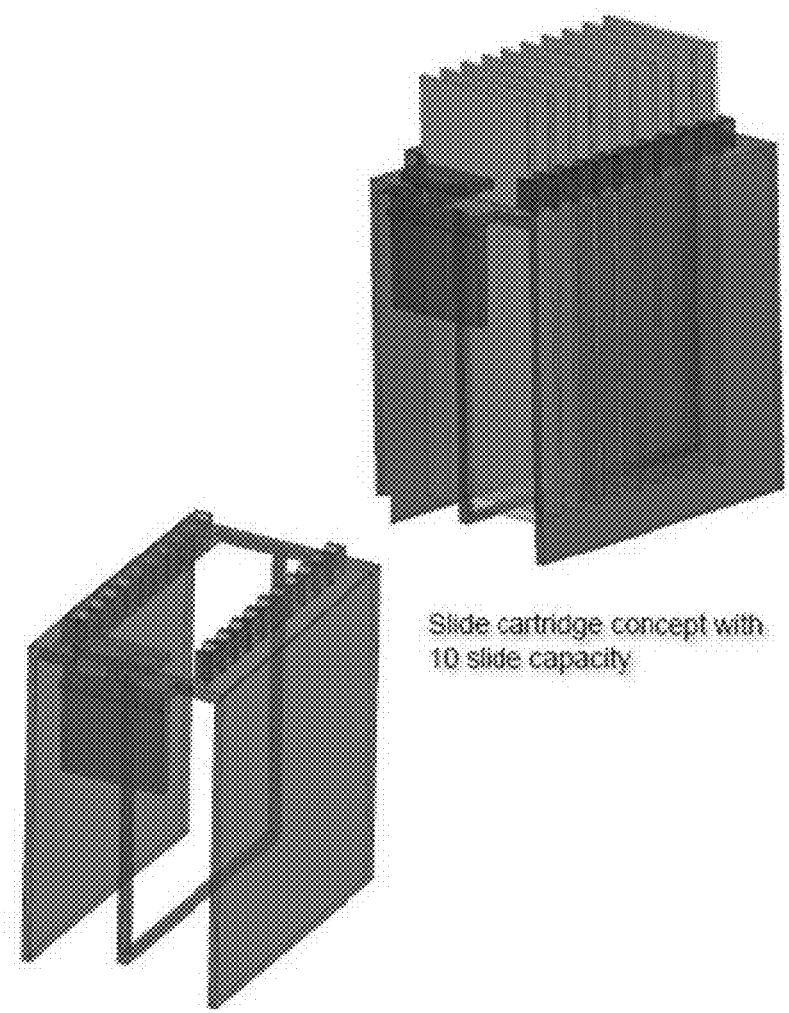
FIG. 1 is an illustration of a cartridge that can be used to hold several substrates at the same time and move the substrates between portions of a staining system or subsystem.

The present disclosure provides methods for carrying out Romanowsky-type stains, specifically Wright-Giemsa stains and May-Grünwald stains, quickly and efficiently. The methods provided herein greatly reduce the overall amount of time required to complete a Wright-Giemsa stain or a May-Grünwald stain of sufficient quality on a biological sample. The subject methods can be applied to manual as well as automated staining procedures.

Definitions

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a sample" includes a plurality of such samples and reference to "the sample" includes reference to one or more samples and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "pure solution" as used herein refers to a solution that is substantially free of other components, e.g., a solution that comprises about 95%, up to about 96%, up to about 97%, up to about 98%, or up to about 99% or greater of a given compound. For example, a "pure solution" of methanol would describe a solution that comprises at least 95%, up to about 96%, up to about 97%, up to about 98%, up to about 99%, or a greater amount of methanol.

The term "reagent" as used herein broadly refers to a chemical compound, a solvent, or a chemical compound dissolved in a solvent to create a solution. For example, the term "reagent" may be used herein to describe a thiazin and/or an eosin dye, a solution comprising a thiazin and/or an eosin dye, or a solvent (e.g., methanol or de-ionized water).

The terms "thiazin," "thiazin compound," and "thiazin dye," as used interchangeably herein, broadly refer to chemical substances comprising a ring of four carbon atoms, one nitrogen atom, and one sulfur atom. Exemplary thiazin compounds include, but are not limited methylene blue, methylene violet, azure A, azure B, azure C, thionin, as well as oxidation products of these compounds.

The terms "eosin," "eosin compound," and "eosin dye," as used interchangeably herein, broadly refer to chemical substances comprising brominated fluorescein. Exemplary eosin compounds include, but are not limited to, eosin Y and eosin B.

The term "normal cells" as used herein describes cells having a clinically ordinary or normal morphology, such as those that would be found in a subject that does not display symptoms of a particular disease or disorder.

The term "abnormal cells" as used herein describes cells having a clinically relevant abnormal morphology, such as those that would be found in a subject suffering from a disease or disorder characterized by abnormal cells that display an altered or deviated morphology.

The term "Wright-Giemsa stain," as used herein, generally refers to a solution comprising thiazin and eosin compounds in various concentrations. Such solutions may be commercially available in concentrated or diluted form, or may be created by dissolving a specified amount of thiazin and/or eosin compounds in a suitable solvent to create such a solution.

The term "May-Grünwald stain," as used herein, generally refers to a solution comprising thiazin and eosin compounds in various concentrations. Such solutions may be commercially available in concentrated or diluted form, or may be created by dissolving a specified amount of thiazin and/or eosin compounds in a suitable solvent to create such a solution.

Methods of Use

The methods of the present disclosure generally find use in staining biological samples for microscopic analysis, such as, e.g., examination of the morphology of different cell types present in a biological sample, in a reduced amount of time. Existing tissue staining techniques generally involve extended periods of reagent incubation time, and are not designed to expedite the staining procedure in order to enable high throughput staining of multiple samples. The present inventors have discovered a method for staining biological samples with a Wright-Giemsa staining reagent or a May-Grünwald staining reagent that greatly reduces the overall period of time required to complete the stain as compared to other known methods. The accelerated staining procedures produce stained samples having similar quality to those produced using other known methods. Furthermore, the accelerated staining methods are highly reproducible, lending themselves to implementation via manual as well as automated formats.

The steps involved with the subject methods include, but are not limited to, applying a biological sample to a substrate, contacting the sample with a fixation reagent, contacting the sample with a Wright-Giemsa staining reagent or a May-Grúnwald staining reagent, and contacting the sample with one or more rinse reagents. The period of time that the sample is contacted with a particular reagent is tightly controlled so that the staining procedure can be carried out in as little time as possible while still maintaining the quality of the stain. In some embodiments, the sample is dried. The steps of the subject methods are described in further detail herein.

Application of Sample to Substrate

A variety of techniques may be used to apply a biological sample to a substrate for use in the subject methods. In some embodiments, a biological sample is applied to the substrate using a drop-wise application procedure, wherein drops of the sample are placed on a substrate. In some embodiments, a biological sample is applied to a substrate by spreading the biological sample in a thin film over the substrate. In some embodiments, following application of the sample to the substrate, a spreading or smearing technique is used to create a thin film of the sample over the surface of the substrate. In some embodiments, the biological sample is dried on the substrate before further steps of the methods are carried out.

In some embodiments, a biological sample is applied to a substrate manually by a technician. In some embodiments, a biological sample is applied to a substrate using automated equipment, such as, e.g., a smearing machine or apparatus. In some embodiments, a biological sample is applied to a substrate using a combination of manual application procedures and automated application procedures, such as, e.g., wherein a technician applies one or more drops of a sample to a substrate, and automated equipment is used to spread the sample over the substrate to create a thin film.

Contacting the Sample with Reagents

Following application of a biological sample to a substrate, the sample is contacted with various reagents in order to carry out the staining procedure and prepare the sample for microscopic analysis. In some embodiments, contacting the sample with a reagent generally involves immersing the substrate in a solution comprising the reagent, e.g., immersing the substrate in a reagent bath. FIG. 1 is an illustration of a cartridge (or slide carrier) that can be used to hold multiple substrates (e.g., microscope slides) at the same time. Such a cartridge may be used to immerse multiple substrates in a reagent bath at the same time. In other embodiments, contacting the sample with a reagent involves applying a sufficient quantity of a solution comprising the reagent to the substrate in order to cover the biological sample on the substrate.

When contacting a sample with a reagent, the substrate may be positioned in any of a variety of different orientations. For example, the substrate may be positioned horizontally, vertically, or may be positioned at an angle with respect to the reagent. In some embodiments, the substrate is positioned horizontally or at an angle and a solution comprising the reagent is applied from above the substrate by dripping, spraying, or otherwise applying the solution over the surface of the substrate. In some embodiments, the substrate is positioned vertically and contacting the sample with a reagent comprises immersing the substrate in a solution comprising the reagent, e.g., immersing the substrate in a reagent bath.

In some embodiments, a combination of reagent application techniques is used to perform the subject methods. For example, in some embodiments, a first reagent is applied to the sample by orienting the substrate vertically and immersing the substrate in a solution comprising the first reagent. Subsequently, the substrate is oriented horizontally or at an angle and a solution comprising another reagent is applied to the sample by dripping, spraying, or otherwise applying the solution over the surface of the substrate. Any of a variety of techniques for contacting a biological sample with a reagent can be combined in any suitable fashion to carry out the subject methods.

In some embodiments, the substrate on which the sample is mounted is held still in the reagent bath during the period of time in which the sample is contacted with the reagent. For example, in some embodiments, the substrate is immersed in a reagent bath and both the substrate and the reagent bath remain motionless for the period of time during which the sample is contacted with the reagent. In certain embodiments, the substrate on which the sample is mounted is not centrifuged, rotated, or subjected to any other movements during the period of time in which the sample is contacted with a particular reagent.

Contact with Fixation Reagent

Following application of the biological sample to the substrate, the sample is contacted with a fixation reagent for a controlled period of time. In some embodiments, the sample is contacted with a fixation reagent for a period of time that ranges from about 15 seconds up to about 60 seconds. In some embodiments, the sample is contacted with a fixation reagent for a period of time that ranges from about 15 seconds up to about 45 seconds. In some embodiments, the sample is contacted with a fixation reagent for a period of time that ranges from about 20 seconds up to about 40 seconds. In some embodiments, the sample is contacted with a fixation reagent for a period of time that ranges from about 25 seconds up to about 35 seconds. In some embodiments, the sample is contacted with a fixation reagent for a period of time that ranges from about 30 seconds up to about 35 seconds.

The inventors of the subject methods have discovered that the overall amount of time required to carry out a Wright-Giemsa or a May-Grünwald staining procedure of sufficient quality on a biological sample can be greatly reduced by contacting the biological sample with a fixation reagent for a period of time ranging from about 20 seconds, up to about 25 seconds, up to about 30 seconds, up to about 35 seconds, up to about 40 seconds, up to about 45 seconds, up to about 50 seconds, up to about 55 seconds, up to about 60 seconds.

Contact with Wright-Giemsa Staining Reagent

Following contact with a fixation reagent, a sample may be contacted with a Wright-Giemsa staining reagent for a controlled period of time. In some embodiments, the sample is contacted with a Wright-Giemsa staining reagent for a period of time that ranges from about 15 seconds up to about 60 seconds. In some embodiments, the sample is contacted with a Wright-Giemsa staining reagent for a period of time that ranges from about 15 seconds up to about 45 seconds. In some embodiments, the sample is contacted with a Wright-Giemsa staining reagent for a period of time that ranges from about 20 seconds up to about 40 seconds. In some embodiments, the sample is contacted with a Wright-Giemsa staining reagent for a period of time that ranges from about 25 seconds up to about 35 seconds. In some embodiments, the sample is contacted with a Wright-Giemsa staining reagent for a period of time that ranges from about 30 seconds up to about 35 seconds.

The inventors of the subject methods have discovered that the overall amount of time required to carry out a Wright-Giemsa staining procedure of sufficient quality on a biological sample can be greatly reduced by contacting the biological sample with a Wright-Giemsa staining reagent for a period of time ranging from about 20 seconds, up to about 25 seconds, up to about 30 seconds, up to about 35 seconds, up to about 40 seconds, up to about 45 seconds, up to about 50 seconds, up to about 55 seconds, up to about 60 seconds.

Contact with May-Grünwald Staining Reagent

Following contact with a fixation reagent, a sample may be contacted with a May-Grúnwald staining reagent for a controlled period of time. In some embodiments, the sample is contacted with a May-Grünwald staining reagent for a period of time that ranges from about 165 seconds up to about 195 seconds. In some embodiments, the sample is contacted with a May-Grünwald staining reagent for a period of time that ranges from about 170 seconds up to about 190 seconds. In some embodiments, the sample is contacted with a May-Grünwald staining reagent for a period of time that ranges from about 175 seconds up to about 185 seconds. In some embodiments, the sample is contacted with a May-Grünwald staining reagent for a period of time that ranges from about 180 seconds up to about 185 seconds.

The inventors of the subject methods have discovered that the overall amount of time required to carry out a May-Grünwald staining procedure of sufficient quality on a biological sample can be greatly reduced by contacting the biological sample with a May-Grúnwald staining reagent for a period of time ranging from about 170 seconds, up to about 175 seconds, up to about 180 seconds, up to about 185 seconds, up to about 190 seconds.

Contact with Rinse Reagent

Following contact with a staining reagent, a sample may be contacted with one or more rinse reagents for a controlled period of time. In some embodiments, the sample is contacted with a first rinse reagent for a period of time that ranges from about 105 seconds up to about 135 seconds. In some embodiments, the sample is contacted with a first rinse reagent for a period of time that ranges from about 110 seconds up to about 130 seconds. In some embodiments, the sample is contacted with a first rinse reagent for a period of time that ranges from about 115 seconds up to about 125 seconds.

The inventors of the subject methods have discovered that the overall amount of time required to carry out a staining procedure of sufficient quality on a biological sample can be greatly reduced by contacting the biological sample with a first rinse reagent for a period of time ranging from about 110 seconds, up to about 115 seconds, up to about 120 seconds, up to about 125 second, or up to about 130 seconds.

In some embodiments, the sample is contacted with a first rinse reagent for a period of time that ranges from about 135 seconds up to about 165 seconds. In some embodiments, the sample is contacted with a first rinse reagent for a period of time that ranges from about 140 seconds up to about 160 seconds. In some embodiments, the sample is contacted with a first rinse reagent for a period of time that ranges from about 145 seconds up to about 155 seconds.

The inventors of the subject methods have discovered that the overall amount of time required to carry out a staining procedure of sufficient quality on a biological sample can be greatly reduced by contacting the biological sample with a first rinse reagent for a period of time ranging from about 110 seconds, up to about 115 seconds, up to about 120 seconds, up to about 125 second, or up to about 130 seconds.

In some embodiments, a sample is contacted with a second rinse reagent for a period of time that ranges from about 5 seconds up to about 45 seconds. In some embodiments, the sample is contacted with a second rinse reagent for a period of time that ranges from about 10 seconds up to about 40 seconds. In some embodiments, the sample is contacted with a second rinse reagent for a period of time that ranges from about 15 seconds up to about 35 seconds. In some embodiments, the sample is contacted with a second rinse reagent for a period of time that ranges from about 20 seconds up to about 30 seconds.

The inventors of the subject methods have discovered that the overall amount of time required to carry out a staining procedure of sufficient quality on a biological sample can be greatly reduced, in some embodiments, by contacting the biological sample with a second rinse reagent for a period of time ranging from about 10 seconds, up to about 15 seconds, up to about 20 seconds, up to about 25 second, up to about 30 seconds, up to about 35 seconds, or up to about 40 seconds.

Drying

In some embodiments, following contacting the sample with the above-described reagents, the sample is dried. Samples can be dried using simple air drying techniques, wherein the substrate is stored in air for a sufficient period of time to allow the sample to dry. In some embodiments, a substrate may be stored in a drying chamber wherein the temperature is elevated in order to facilitate the drying process. Drying chambers may also employ circulating air produced by, e.g., one or more fans, in order to facilitate the drying process.

Manual and/or Automated Performance of Methods

The subject methods may be performed manually by one or more technicians, or may be performed automatically, using automated equipment that is designed and/or programmed to carry out the steps of the subject methods. In some embodiments, the subject methods may be performed through a combination of manual performance by technicians and automated performance by equipment.

For example, in some embodiments, the subject methods are entirely performed manually by technicians. In other embodiments, the subject methods are performed entirely by automated equipment that has been designed and/or programmed to carry out the steps of the subject methods in a particular order. In some embodiments, certain steps of the subject methods are performed by technicians, while certain other steps of the subject methods are performed by automated equipment that has been designed and/or programmed to carry out the designated steps. Any combination of manual and/or automated performance may be used to carry out the subject methods.

Figure 2:
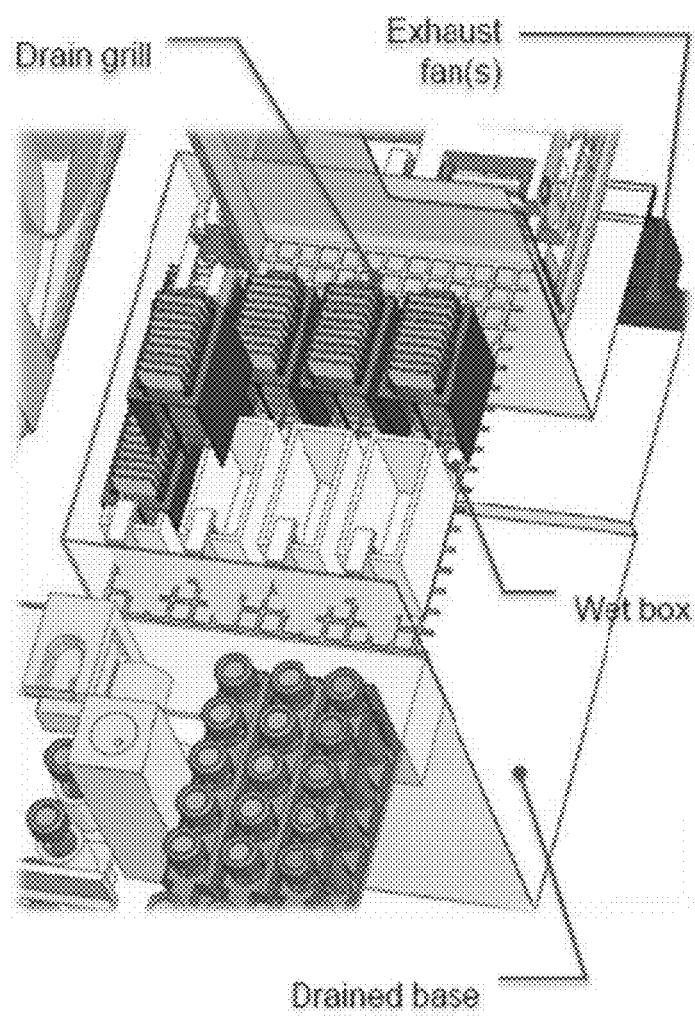
FIG. 2 is an illustration of a portion of a staining system showing several reagent bath containers and several cartridges holding multiple substrates.
Figure 3:
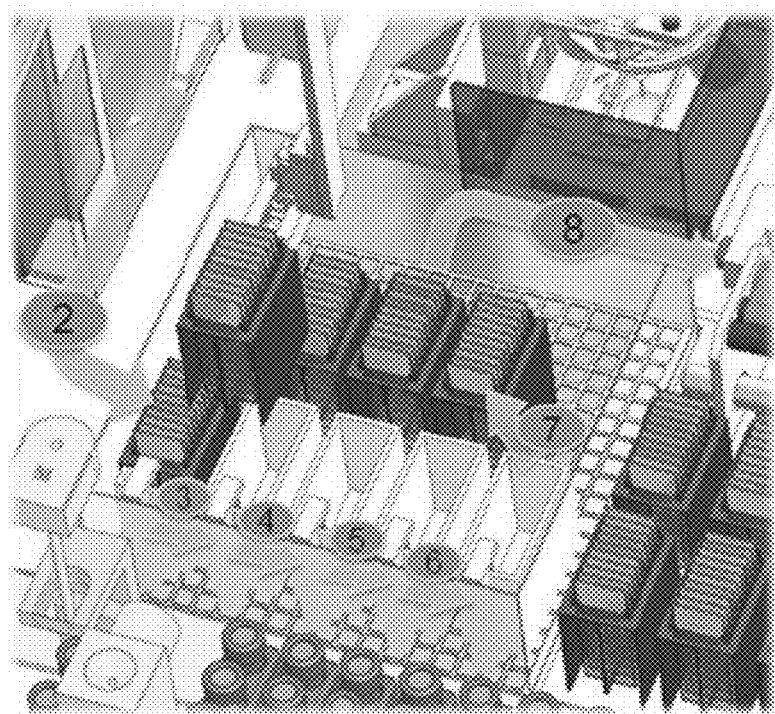
FIG. 3 is illustration of a staining system showing movement of a cartridge holding multiple substrates through several reagent baths, followed by movement to a drying area.

FIG. 2 shows an illustration of an automated staining system comprising multiple reagent baths and multiple cartridges, each cartridge holding multiple samples. In use, the automated system moves a cartridge between the reagent baths and immerses the cartridges in each reagent bath for a specified period of time. FIG. 3 shows an illustration of a staining system wherein a cartridge enters the system, moves between several reagent baths, moves to a drying area, and then moves out of the automated staining system.

Biological Samples

The subject methods may generally be performed on any of a variety of biological samples in order to facilitate microscopic analysis of a sample. Exemplary biological samples include, but are not limited to, biological fluids, e.g., blood samples and bone marrow samples.

Blood Samples

Blood samples for use with the subject methods may be obtained from a subject by any suitable method, including but not limited to withdrawing blood from a subject using a needle and syringe. In some embodiments, blood samples may be collected from a subject using a finger-stick technique, wherein the subject's skin is punctured and a sufficient amount of blood is "milked" or expressed from the puncture. Blood samples suitable for use in the subject methods include both venous and arterial blood samples. Any blood sample collection procedure may be readily adapted for use with the subject methods.

Bone Marrow Samples

Bone marrow samples for use with the subject methods may be obtained by any suitable method, including but not limited to needle aspiration. Bone marrow aspiration samples may be collected using, e.g., an aspiration needle that is inserted through the subject's skin and then advanced through the outer portion of a bone and into the bone marrow cavity. Once the needle has been placed inside the bone marrow cavity, a syringe attached to the needle is used to aspirate a liquid sample comprising bone marrow. Any bone marrow sample collection procedure may be readily adapted for use with the subject methods.

Substrates

The subject methods involve applying a biological sample to a substrate. Substrates amenable for use with the subject methods are generally rigid or semi-rigid structures made of transparent material. Such materials include, but are not limited to plastic, glass, and/or quartz. In some embodiments, the substrate is a microscope slide made of any suitable material and having any suitable geometry.

In some embodiments, the length of the substrate ranges in size from about 20 mm, up to about 25 mm, up to about 30 mm, up to about 35 mm, up to about 40 mm, up to about 45 mm, up to about 50 mm, up to about 55 mm, up to about 60 mm, up to about 65 mm, up to about 70 mm, up to about 75 mm, up to about 80 mm. In some embodiments, the width of the substrate ranges in size from about 20 mm, up to about 25 mm, up to about 30 mm, up to about 35 mm, up to about 40 mm, up to about 45 mm, up to about 50 mm, up to about 55 mm, up to about 60 mm, up to about 65 mm, up to about 70 mm, up to about 75 mm, up to about 80 mm. In some embodiments, the thickness of the substrate ranges from about 0.5 mm, up to about 0.8 mm, up to about 1 mm, up to about 1.2 mm, up to about 1.5 mm. In some embodiments, the substrate is a standard microscope slide that is approximately 75 mm in length, 25 mm in width, and 1 mm thick.

In some embodiments, the substrate comprises one or more surface coatings or surface treatments, such as poly-L-lysine or silane treatment. In some embodiments, the substrate comprises a surface coating or surface treatment that renders at least a portion of the substrate opaque or semi-opaque, such as a frosting or a glazing treatment. In some embodiments, the substrate comprises an area that can be used for labeling, such as, e.g., an end or corner region upon which a suitable label can be placed. In some embodiments, a substrate is labeled using labeling equipment, such as, e.g., equipment that applies a label to a surface of the substrate, etches and/or marks the substrate to create a label, or prints or applies ink and/or any other suitable marking material to a surface of the substrate to create a label.

In some embodiments, the substrate may be labeled manually, e.g., wherein a technician manually places a label on the substrate, or wherein a technician writes on or otherwise marks the substrate to create a label. In some embodiments, a technician utilizes labeling equipment to label a substrate. In some embodiments, a substrate is labeled using automated labeling equipment. In such embodiments, labeling information may be provided to the automated labeling equipment by a computer program.

Reagents

The subject methods involve contacting a biological sample with a variety of different reagents, which are described in more detail below. The specific temperature of the reagents described below does not impact the subject methods. The subject methods may be performed using reagents at a temperature ranging from about 2-8° C., up to about 15° C., up to about 20° C., up to about 25° C., or up to about 30° C. without impacting the quality of the stain produced.

Fixation Reagents

The subject methods involve contacting a biological sample with a fixation reagent. Suitable fixation reagents generally include organic solvents, such as alcohols or acetone, which remove lipids and dehydrate cells. Exemplary fixation reagents include methanol, ethanol, acetone, solutions comprising these reagents, and mixtures thereof. In some embodiments, a solution of pure methanol is used as a fixation reagent. In some embodiments, a solution of pure acetone is used as a fixation reagent. In some embodiments, a solution of pure ethanol is used as a fixation reagent. In some embodiments, a solution of 95% ethanol and 5% glacial acetic acid is used as a fixation reagent. In some embodiments, a solution of 50% methanol and 50% acetone is used as a fixation reagent. In some embodiments, a solution of 50% methanol and 50% ethanol is used as a fixation reagent.

Wright-Giemsa Staining Reagent

In some embodiments, the subject methods involve contacting a biological sample with a Wright-Giemsa staining reagent. Wright-Giemsa staining reagents generally comprise varying amounts of both Wright's stain and Giemsa stain compounds, which both comprise thiazin and eosin dyes. The thiazin and eosin dyes in a Wright-Giemsa staining reagent bind to and color various components of biological samples so that they can be visualized under microscopic examination. Thiazin dyes generally include, but are not limited to, methylene blue, methylene violet, azure A, azure B, azure C, and thionin. Thiazin dyes also include oxidation products of these compounds. Eosin dyes generally include, but are not limited to, eosin Y and eosin B. Wright-Giemsa staining reagents and staining stock solutions comprising various amounts of thiazin and eosin compounds are commercially available to the public from a variety of sources and suppliers. In some embodiments, a Wright-Giemsa staining stock solution may also comprise glycerin.

In some embodiments of the subject methods, a commercially-available Wright-Giemsa staining stock solution is used as the Wright-Giemsa staining reagent without any further dilution or modification. In some embodiments, a Wright-Giemsa staining stock solution is diluted prior to use in the subject methods by mixing the staining stock solution with a suitable solvent. In some embodiments, a Wright-Giemsa staining stock solution is diluted with an organic solvent, e.g., methanol, to produce a staining solution of a particular concentration for use in the subject methods. In some embodiments, a Wright-Giemsa staining stock solution is diluted with an aqueous solvent, e.g., de-ionized water or phosphate buffer, to produce a staining solution of a particular concentration for use in the subject methods.

In some embodiments, a Wright-Giemsa staining reagent is created by mixing a desired amount of thiazin and eosin compounds together in a suitable solvent to create a solution. In some embodiments, a commercially-available Wright-Giemsa powder, comprising specified amounts of thiazin and eosin compounds, is mixed with a suitable solvent to create a solution that can be used as a Wright-Giemsa staining reagent in the subject methods.

In some embodiments, the concentration of thiazin dye in the Wright-Giemsa staining solution ranges from less than about 1%, up to about 5%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, or up to about 90%. In some embodiments, the concentration of eosin dye in the Wright-Giemsa staining solution ranges from less than about 1%, up to about 5%, about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, or up to about 90%.

As discussed above, Wright-Giemsa staining stock solutions are commercially available to the public from a variety of suppliers, including, e.g., Wright-Giemsa Stain Solution, catalog number 08711, sold under the trade name ACCUSTAIN® by Sigma-Aldrich. Wescor staining solutions are available through Wecor, Inc. and are sold under the name Aerospray Hematology Pro Stain. These reagents are available in the form of Buffered Rinse 5L (pH 6.8 and pH 7.2), Thiazin 500 mL, Eosin 500 mL and Fixative 500 mL (Aerofix, methanol). Methanol, Wright Giemsa stain, and phosphate buffer (pH 6.8 and pH 7.2) reagents are also available through VWR Inc (VWR.com) under the brand name Harleco Hematology Stains and Reagents, EMD Millipore or EMD Chemicals, Inc.

In some embodiments, the concentration of glycerin in the Wright-Giemsa staining stock solution ranges from less than about 1% to up to about 5%, up to about 8%, up to about 10%, up to about 12%, or up to about 15%.

May-Grünwald Staining Reagent

In some embodiments, the subject methods involve contacting a biological sample with a May-Grünwald staining reagent. May-Grünwald staining reagents generally comprise varying amounts of thiazin and eosin dyes. The thiazin and eosin dyes in a May-Grünwald staining reagent bind to and color various components of biological samples so that they can be visualized under microscopic examination. Thiazin dyes generally include, but are not limited to, methylene blue, methylene violet, azure A, azure B, azure C, and thionin. Thiazin dyes also include oxidation products of these compounds. Eosin dyes generally include, but are not limited to, eosin Y and eosin B. May-Grünwald staining reagents and staining stock solutions comprising various amounts of thiazin and eosin compounds are commercially available to the public from a variety of sources and suppliers. In some embodiments, a May-Grünwald staining stock solution may also comprise glycerin.

In some embodiments of the subject methods, a commercially-available May-Grünwald staining stock solution is used as the May-Grünwald staining reagent without any further dilution or modification. In some embodiments, a May-Grünwald staining stock solution is diluted prior to use in the subject methods by mixing the staining stock solution with a suitable solvent. In some embodiments, a May-Grünwald staining stock solution is diluted with an organic solvent, e.g., methanol, to produce a staining solution of a particular concentration for use in the subject methods. In some embodiments, a May-Grünwald staining stock solution is diluted with an aqueous solvent, e.g., de-ionized water or phosphate buffer, to produce a staining solution of a particular concentration for use in the subject methods.

In some embodiments, a May-Grünwald staining reagent is created by mixing a desired amount of thiazin and eosin compounds together in a suitable solvent to create a solution. In some embodiments, a commercially-available May-Grünwald powder, comprising specified amounts of thiazin and eosin compounds, is mixed with a suitable solvent to create a solution that can be used as a May-Grünwald staining reagent in the subject methods.

In some embodiments, the concentration of thiazin dye in the May-Grünwald staining solution is about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, or up to about 90%. In some embodiments, the concentration of eosin dye in the May-Grünwald staining solution is about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, or up to about 90%.

As discussed above, May-Grünwald staining stock solutions are commercially available to the public from a variety of suppliers, including, e.g., May-Grünwald Stain, catalog number 89027, sold by Thermo Scientific.

In some embodiments, the concentration of glycerin in the May-Grünwald staining stock solution ranges from less than about 1% up to about 5%, up to about 8%, up to about 10%, up to about 12%, or up to about 15%.

Rinse Reagents

The subject methods generally involve contacting a biological sample with one or more suitable rinse reagents. Rinse reagents suitable for use with the subject methods include, but are not limited to, de-ionized water, phosphate buffer solutions comprising varying concentrations of monobasic potassium phosphate and dibasic sodium phosphate dissolved in a suitable aqueous solvent, e.g., de-ionized water, and pH adjusted to a target pH value. Addition of a rinse reagent having a specified pH value to the sample ionizes the thiazin and eosin compounds in the staining reagent and helps them to develop various degrees of coloration, which facilitates microscopic examination of the sample.

In some embodiments, the concentration of monobasic potassium phosphate in the phosphate buffer ranges from 0% up to about 5%, or up to about 45%, up to about 46%, up to about 47%, up to about 48%, up to about 49%, up to about 50%, up to about 51%, wherein the % is a w/w %. In some embodiments, the concentration of dibasic sodium phosphate in the phosphate buffer ranges from 0% up to about 5%, or up to about 49%, up to about 50%, up to about 51%, up to about 52%, up to about 53%, up to about 54%, up to about 55%, wherein the % is a w/w %.

In some embodiments, the pH of the phosphate buffer ranges from about 5.0, up to about 5.2, up to about 5.4, up to about 5.6, up to about 5.8, up to about 6.0, up to about 6.1, up to about 6.2, up to about 6.3, up to about 6.4, up to about 6.5, up to about 6.6, up to about 6.7, up to about 6.8, up to about 6.9, up to about 7.0, up to about 7.1, up to about 7.2, up to about 7.3, up to about 7.4, up to about 7.5, up to about 7.6, up to about 7.8, up to about 7.9, up to about 8.0, up to about 8.2, up to about 8.4, up to about 8.6, up to about 8.8, up to about 9.0 pH units.

In some embodiments, commercially-available phosphate buffer is used as a rinse reagent. Phosphate buffer is commercially available to the public from a variety of suppliers, including, e.g., Wright Stain Phosphate Buffer pH 6.8, catalog number 24989, from Polysciences, Inc. Wescor staining solutions are available through Wescor, Inc. and are sold under Aerospray Hematology Pro Stain. The phosphate buffers are available in the form of Buffered Rinse 5L (pH 6.8 and pH 7.2).

In some embodiments, the subject methods involve the use of a high salt phosphate buffer as a rinse reagent. By "high salt phosphate buffer" is meant a phosphate buffer solution comprising from about 5.0 to about 5.5 grams of dibasic sodium phosphate and from about 5.0 to about 5.5 grams of monobasic potassium phosphate per liter of solvent.

An example formulation of a high salt phosphate buffer that can be used in some embodiments of the present methods is provided in Table 1, below:

TABLE 1

Example of high salt phosphate buffer formulation

| Component Name | Units of Measurement | Quantity (per Liter) |
|---|---|---|
| High Salt Phosphate Buffer | | |
| Water for in vitro Mfg. | LT | 1 |
| Sodium Phosphate Dibasic | g | 5.338 |
| Potassium Phosphate Monobasic | g | 5.193 |
| Proclin 300 | g | 0.6 |
| Proclin 950 | g | 0.8 |
| Characteristics | | |
| pH | | 6.8 ± 0.20 |
| Osmolarity | | 10 ± 3 mOsm |

In some embodiments, the subject methods involve the use of a low salt phosphate buffer as a rinse reagent. By "low salt phosphate buffer" is meant a phosphate buffer solution comprising from about 0.1 to about 0.5 grams of dibasic sodium phosphate and from about 0.1 to about 0.5 grams of monobasic potassium phosphate per liter of solvent.

An example formulation of a low salt phosphate buffer that can be used in some embodiments of the present methods is provided in Table 2, below:

TABLE 2

Example of low salt phosphate buffer formulation

| Component Name | Units of Measurement | Quantity (per Liter) |
|---|---|---|
| Low Salt Phosphate Buffer | | |
| Water for in vitro Mfg. | LT | 1 |
| Sodium Phosphate Dibasic | g | 0.235 |
| Potassium Phosphate Monobasic | g | 0.229 |
| Proclin 300 | g | 0.6 |
| Proclin 950 | g | 0.8 |
| Characteristics | | |
| pH | | 6.8 ± 0.20 |
| Osmolarity | | 10 ± 3 mOsm |

Both low salt and high salt phosphate buffer solutions may, in some embodiments, also contain various additional components, such as, e.g., antimicrobial agents such as, e.g., Proclin 300, Proclin 950, and the like in suitable quantities, such as, e.g., approximately 0.5 up to about 0.6, up to about 0.7, up to about 0.8, up to about 0.9, up to about 1.0 gram per liter of solvent.

Figure 4:
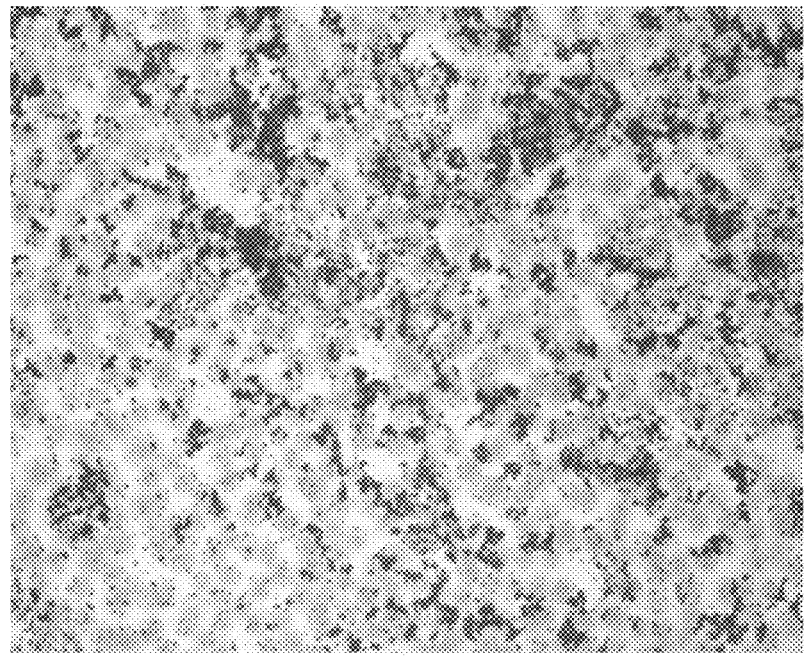
FIG. 4: Panel A is a microscopic image of a sample that was stained using a high salt phosphate buffer. Panel B is a microscopic image of a sample that was stained using a low salt phosphate buffer.
Figure 4:
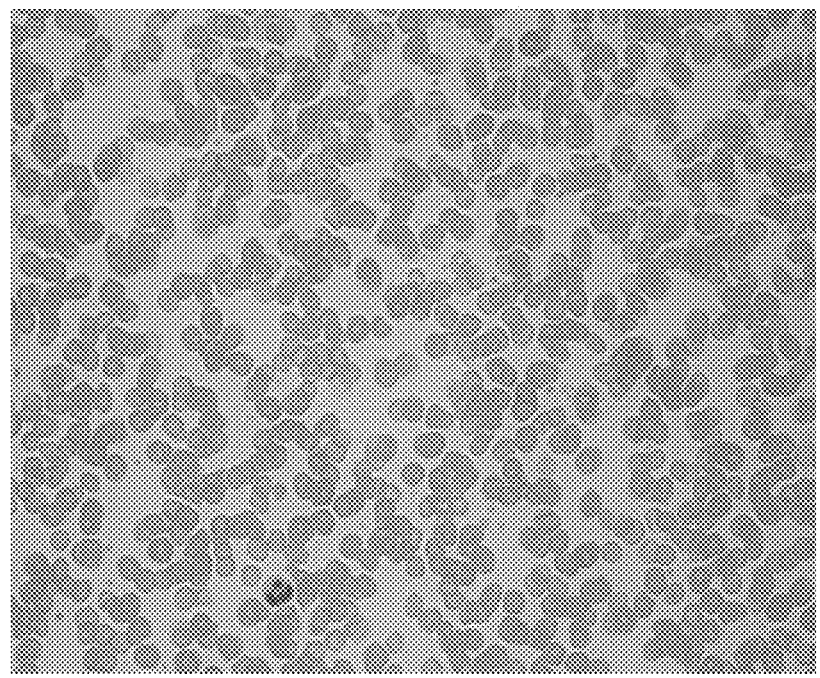

Additional examples of rinse reagents include, but are not limited to, de-ionized water, phosphate buffered saline solution, and the like. FIG. 4, panel A shows a microscopic image of a sample that was stained and then rinsed with a high salt phosphate buffer, and panel B shows a microscopic image of a sample that was stained and then rinsed with a low salt phosphate buffer. As can be seen, reducing the salt concentration in the phosphate buffer reduced the amount of stain precipitation in this embodiment.

Figure 5:
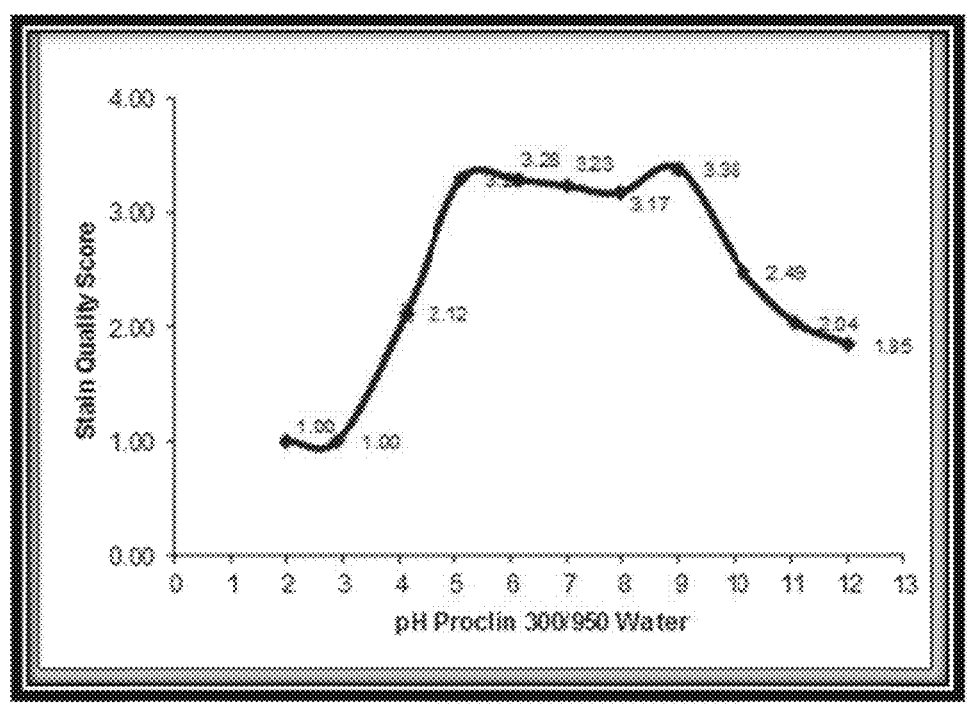
FIG. 5 is a graph showing stain quality as a function of the pH of the rinse reagent used in a May-Grünwald staining method of the present disclosure.

FIG. 5 shows a graph of the stain quality as a function of the pH value of the rinse solution used to perform a May-Grünwald stain. As can be seen from the graph, the stain quality is relatively constant over a pH range of 5.0 up to 9.0 for the rinse reagent.

Figure 6:
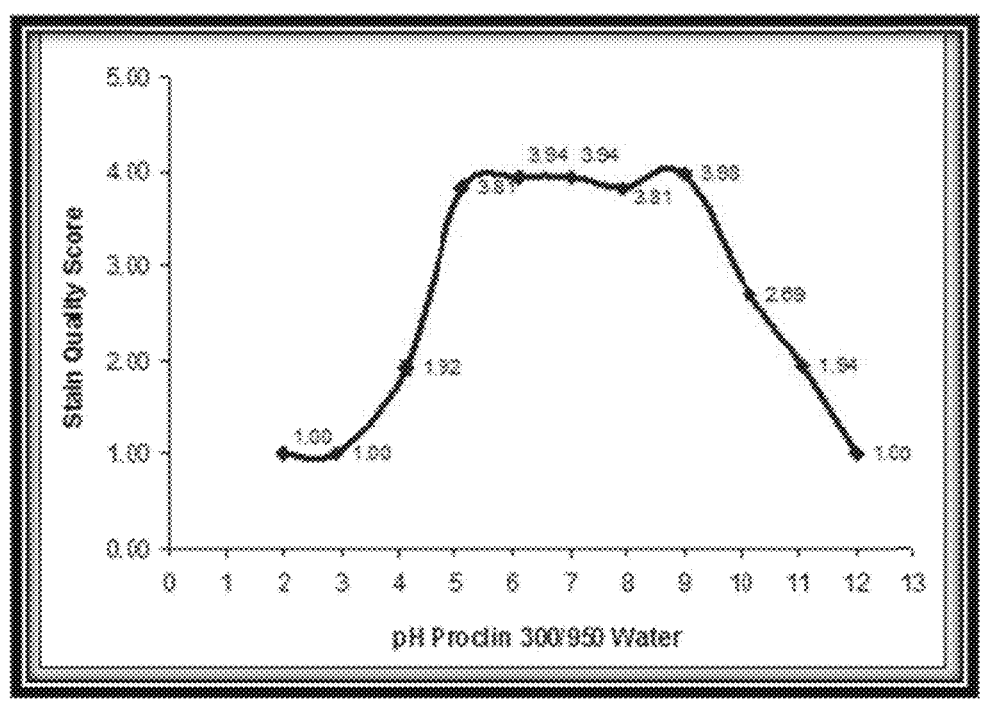
FIG. 6 is a graph showing stain quality as a function of the pH of the rinse reagent used in a Wright-Giemsa staining method of the present disclosure.

FIG. 6 shows a graph of the stain quality as a function of the pH value of the rinse solution used to perform a Wright-Giemsa stain. As can be seen from the graph, the stain quality is relatively constant over a pH range of 5.0 up to 9.0 for the rinse reagent.

Additional Embodiments

In some embodiments, the present disclosure provides an automated staining system for performing a stain on one or more samples, comprising: a sample application subsystem that applies a sample to a substrate; a fixation reagent bath; a staining reagent bath; one or more rinse reagent baths; a sample transfer subsystem for moving the substrate from the sample application subsystem, to the fixation reagent bath, to the staining reagent bath, and then to the one or more rinse reagent baths; and a computer readable storage medium (e.g., a digital storage medium) comprising instructions executable by at least one processing device that, when executed, cause the processing device to control the sample transfer subsystem such that the sample transfer subsystem places the one or more samples into the reagent baths for a controlled period of time.

In some embodiments, the sample is placed in the fixation reagent bath for a period of time ranging from about 15 seconds, up to about 20 seconds, up to about 25 seconds, up to about 30 seconds, up to about 35 seconds, up to about 40 seconds, up to about 45 seconds, up to about 50 seconds, up to about 55 seconds, up to about 60 seconds. In some embodiments, the fixation reagent is methanol.

In some embodiments, the sample is placed in a Wright-Giemsa staining reagent bath for a period of time ranging from about 15 seconds, up to about 20 seconds, up to about 25 seconds, up to about 30 seconds, up to about 35 seconds, up to about 40 seconds, up to about 45 seconds, up to about 50 seconds, up to about 55 seconds, up to about 60 seconds. In some embodiments, the Wright-Giemsa staining reagent comprises methanol.

In some embodiments, the sample is placed in a May-Grünwald staining reagent bath for a period of time ranging from about 165 seconds, up to about 170 seconds, up to about 175 seconds, up to about 180 seconds, up to about 185 seconds, up to about 190 seconds, or up to about 195 seconds. In some embodiments, the May-Grünwald staining reagent comprises methanol.

In some embodiments, the sample is placed in a first rinse reagent bath for a period of time ranging from about 105 seconds, up to about 110 seconds, up to about 115 seconds, up to about 120 seconds, up to about 125 seconds, up to about 130 seconds, up to about 135 seconds, up to about 140 seconds, up to about 145 seconds, up to about 150 seconds, up to about 155 seconds, up to about 160 seconds, up to about 165 seconds. In some embodiments, the first rinse reagent comprises de-ionized water. In some embodiments, the first rinse reagent is a phosphate buffer. In some embodiments, the first rinse reagent is a low salt phosphate buffer or a high salt phosphate buffer.

In some embodiments, the phosphate buffer has a pH value ranging from about 5.0 up to about 9.0 pH units. In some embodiments, the phosphate buffer has a pH value ranging from about 6.5 up to about 7.2 pH units.

In some embodiments, a sample is placed in a second rinse reagent bath for a period of time ranging from about 5 seconds, up to about 10 seconds, up to about 15 seconds, up to about 20 seconds, up to about 25 seconds, up to about 30 seconds, up to about 35 seconds, up to about 40 seconds, up to about 45 seconds. In some embodiments, the second rinse reagent comprises de-ionized water. In some embodiments, the second rinse reagent is a phosphate buffer. In some embodiments, the second rinse reagent is a low salt phosphate buffer or a high salt phosphate buffer.

In some embodiments, the phosphate buffer has a pH value ranging from about 5.0 up to about 9.0 pH units. In some embodiments, the phosphate buffer has a pH value ranging from about 6.5 up to about 7.2 pH units.

In some embodiments, the sample is placed in a drying chamber. In some embodiments, the substrate is a glass microscope slide. In some embodiments, the sample is a biological fluid. In some embodiments, the sample is a blood sample. In some embodiments, the sample is a bone marrow sample.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods

The following materials and methods were used to carry out the examples below.

Stain Quality Scoring Index

In order to provide an objective assessment of the quality of a stain produced from a given staining procedure, the present inventors created a Stain Quality Scoring Index. The numbers in the scoring index range from 1 to 4, wherein 1 is unacceptable quality, 2 is borderline quality, 3 is acceptable quality, and 4 is optimal quality. "Unacceptable" describes a stain wherein the observer cannot differentiate white blood cell features (such as cytoplasmic granules) and cannot perform an accurate manual differential count. "Borderline" describes a stain wherein the observer can differentiate most white blood cell features but may or may not be able to perform an accurate manual differential count. "Acceptable" describes a stain wherein all white blood cells are appropriately stained and the observer can perform an accurate manual differential count on both normal and abnormal cells. "Optimal" describes a stain having ideal stain quality that allows for an easy and accurate manual differential count on both normal and abnormal cell types.

Stained samples were microscopically examined by medical technicians and pathologists and were scored in a variety of general categories, such as staining consistency across the monolayer and stain integrity (inclusion of precipitates, dust, staining artifacts, cells washed away or damaged, etc.), as well as a variety of specific categories, including, e.g., an assessment of the stain quality on neutrophils, lymphocytes, monocytes, eosinophils, basophils, erythrocytes, promyelocytes, myelocytes, metamyelocytes, dohle bodies, howell-jolly bodies, large platelets, and the like present in the sample. Assigned numerical scores were then used to compare the quality of stains produced by different staining procedures and to evaluate the reproducibility of staining procedures.

Example 1

Acceptability of Accelerated Wright-Giemsa Staining Procedure with Normal Cells

An accelerated Wright-Giemsa staining procedure was developed wherein a sample was applied to a substrate and contacted with methanol as a fixation reagent for 30 seconds, followed by contact with a Wright-Giemsa staining reagent for 30 seconds, followed by contact with phosphate buffer at pH 6.8 for 120 seconds, followed by contact with de-ionized water for 15 seconds, followed by air drying. A sample containing normal cells (i.e., cells with clinically normal morphology) was subjected to this staining procedure and evaluated by 14 different individuals experienced in examining hematology samples. These individuals used the Stain Quality Scoring Index described above to assign numerical scores to the sample in a variety of categories. The numerical scores in each category were then used to create an overall average numerical score for the sample.

In parallel, the same individuals also performed a standard hematology stain on the same sample using their own preferred procedure. The standard staining procedures generally involved longer reagent exposure times for each of the reagents as compared to the accelerated staining procedure described above. The samples that were stained using the standard staining procedure were also evaluated using the Stain Quality Scoring Index and assigned an overall average numerical score.

The results from the analysis of the two samples that underwent different staining procedures were then compared for each of the evaluating individuals. The data are provided in Table 3, below.

TABLE 3

Comparison of numerical score assigned to normal cells stained with standard staining procedure and accelerated Wright-Giemsa staining procedure.

| | Individual | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Standard Staining Procedure | 3.8 | 3.3 | 3.9 | n/a | 3.9 | 3.3 | 3.8 | 2.0 | 3.9 | 3.6 | 4.0 | 2.7 | 2.6 | 3.7 |
| Accelerated Wright-Giemsa Staining Procedure | 3.8 | 4.0 | 4.0 | 3.8 | 3.3 | n/a | 3.8 | 3.0 | 4.0 | 3.8 | 4.0 | 3.9 | 3.4 | 3.8 |

Example 2

Acceptability of Accelerated Wright-Giemsa Staining Procedure with Abnormal Cells An accelerated Wright-Giemsa staining procedure was developed wherein a sample was applied to a substrate and contacted with methanol as a fixation reagent for 30 seconds, followed by contact with a Wright-Giemsa staining reagent for 30 seconds, followed by contact with phosphate buffer at pH 6.8 for 120 seconds, followed by contact with de-ionized water for 15 seconds, followed by air drying. A sample containing abnormal cells (i.e., cells with clinically abnormal morphology) was subjected to this staining procedure and evaluated by 14 different individuals experienced in examining hematology samples. These individuals used the Stain Quality Scoring Index described above to assign numerical scores to the sample in a variety of categories. The numerical scores in each category were then used to create an overall average numerical score for the sample.

In parallel, the same individuals also performed a standard hematology stain on the same sample using their own preferred procedure. The standard staining procedures generally involved longer reagent exposure times for each of the reagents as compared to the accelerated staining procedure described above. The samples that were stained using the standard staining procedure were also evaluated using the Stain Quality Scoring Index and assigned an overall average numerical score.

The results from the analysis of the two samples that underwent different staining procedures were then compared for each of the evaluating individuals. The data are provided in Table 4, below.

TABLE 4

Comparison of numerical score assigned to abnormal cells stained with standard staining procedure and accelerated Wright-Giemsa staining procedure.

| | Individual | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Standard Staining Procedure | 2.0 | 3.3 | 3.4 | n/a | 2.1 | 3.1 | 2.9 | 2.0 | 2.8 | 3.6 | 3.8 | 2.4 | 2.9 | 3.0 |
| Accelerated Wright-Giemsa Staining Procedure | 3.6 | 4.0 | 4.0 | 4.0 | 2.8 | n/a | 2.3 | 3.8 | 4.0 | 3.7 | 3.6 | 2.9 | 1.5 | 3.4 |

Example 3

Reproducibility of Accelerated Wright-Giemsa and May-Grünwald Staining Procedure with Normal Cells The reproducibility of the accelerated Wright-Giemsa staining procedure described above in Examples 1 and 2 was evaluated by repeatedly performing the staining procedure on 15 separate days. A sample of normal cells was stained in triplicate on each day using the accelerated procedure, and the samples were assessed for the staining quality on erythrocytes, eosinophilic granules, basophilic granules, leukocyte nuclei, leukocyte cytoplasm, nutrophilic granules, and platelets using the Stain Quality Scoring Index. The results are summarized below in Table 5.

Figure 7:
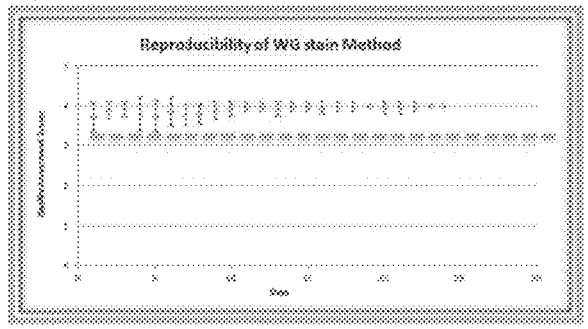
FIG. 7: Panel A is a graph showing the reproducibility of a Wright-Giemsa staining method that was performed over a period of days. Panel B is a graph showing the reproducibility of a May-Grünwald staining method that was performed over a period of days.
Figure 7:
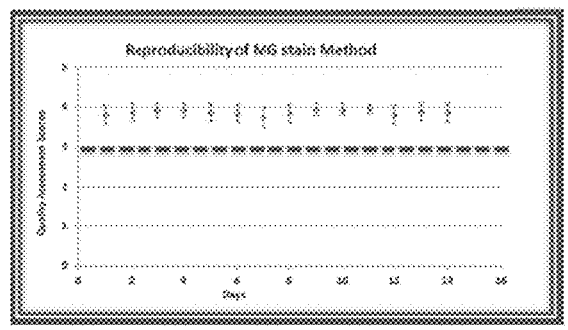

The reproducibility of the accelerated Wright-Giemsa staining procedure was also tested by repeated staining a number of samples over a period of days and plotting the observed stain quality score on each day. The results are summarized in FIG. 7, panel A.

The reproducibility of the accelerated May-Grünwald staining procedure was also tested by repeated staining a number of samples over a period of days and plotting the observed stain quality score on each day. The results are summarized in FIG. 7, panel B.

Figure 8:
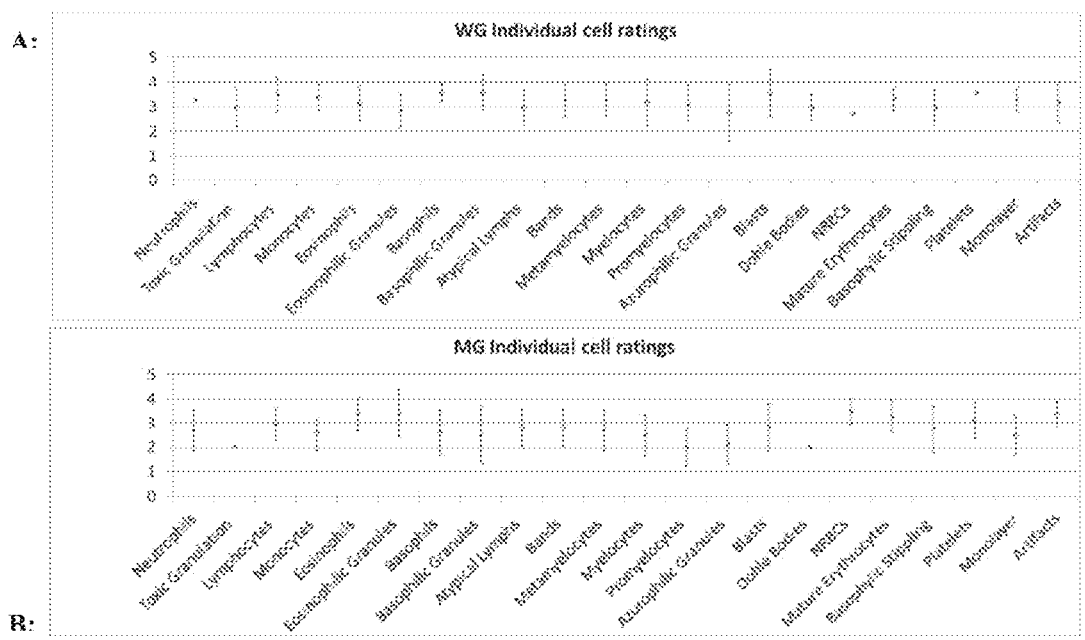
FIG. 8: Panel A is a graph showing the numerical score of cell by cell rating for a number of samples that were stained using a Wright-Giemsa staining method. Panel B is a graph showing the numerical score of cell by cell rating for a number of samples that were stained using a May-Grünwald staining method.

FIG. 8, panel A shows the individual cell ratings for samples that were stained using an accelerated Wright-Giemsa staining procedure of the present disclosure. Panel B shows the individual cell ratings for samples that were stained using an accelerated May-Grünwald staining procedure of the present disclosure. The results indicate that the staining procedures produce highly reproducible staining quality for the cells types that were examined.

TABLE 5

Repeatability data from normal samples stained using accelerated Wright-Giemsa staining procedure.

| Repeatability Results Normal Cells | Day 1 Slide 1 | Day 1 Slide 2 | Day 1 Slide 3 | Day 2 Slide 1 | Day 2 Slide 2 | Day 2 Slide 3 | Day 3 Slide 1 | Day 3 Slide 2 | Day 3 Slide 3 |
|---|---|---|---|---|---|---|---|---|---|
| Erythrocytes | 4 | 4 | 4 | 4 | 4 | 4 | 3 | 4 | 4 |
| Eosinophilic Granules | 4 | 4 | N/A | 4 | 4 | 4 | 1 | 4 | 4 |
| Basophilic Granules | 4 | 4 | 4 | N/A | N/A | 4 | N/A | N/A | 4 |
| Leukocyte Nuclei | 4 | 4 | 4 | 4 | 4 | 4 | 3 | 4 | 4 |
| Leukocyte Cytoplasm | 4 | 4 | 4 | 4 | 4 | 4 | 1 | 4 | 4 |
| Nutrophilic Granules | 4 | 4 | 4 | 4 | 4 | 4 | 1 | 4 | 4 |
| Platelets | 4 | 4 | 4 | 4 | 4 | 4 | 3 | 4 | 4 |
| | Day 4 Slide 1 | Day 4 Slide 2 | Day 4 Slide 3 | Day 5 Slide 1 | Day 5 Slide 2 | Day 5 Slide 3 | Day 6 Slide 1 | Day 6 Slide 2 | Day 6 Slide 3 |
| Erythrocytes | 4 | 4 | 4 | 4 | 4 | 4 | 4 | 4 | 4 |
| Eosinophilic Granules | 4 | 4 | 4 | 4 | 4 | 4 | 4 | 4 | 4 |
| Basophilic Granules | N/A | N/A | N/A | 4 | 4 | 4 | 4 | 4 | 4 |
| Leukocyte Nuclei | 4 | 4 | 4 | 4 | 4 | 4 | 4 | 4 | 4 |
| Leukocyte Cytoplasm | 4 | 4 | 4 | 4 | 4 | 4 | 4 | 4 | 4 |
| Nutrophilic Granules | 4 | 4 | 4 | 4 | 4 | 4 | 4 | 4 | 4 |
| Platelets | 4 | 4 | 4 | 4 | 4 | 4 | 4 | 4 | 4 |
| | Day 7 Slide 1 | Day 7 Slide 2 | Day 7 Slide 3 | Day 8 Slide 1 | Day 8 Slide 2 | Day 8 Slide 3 | Day 9 Slide 1 | Day 9 Slide 2 | Day 9 Slide 3 |
| Erythrocytes | 4 | 4 | 4 | 4 | 4 | 4 | 4 | 4 | 4 |
| Eosinophilic Granules | 4 | 4 | 4 | 4 | 4 | 4 | 4 | 4 | 4 |
| Basophilic Granules | 4 | 4 | 4 | N/A | N/A | N/A | N/A | N/A | 4 |
| Leukocyte Nuclei | 4 | 4 | 4 | 4 | 4 | 4 | 4 | 4 | 4 |
| Leukocyte Cytoplasm | 4 | 4 | 4 | 4 | 4 | 4 | 4 | 4 | 4 |
| Nutrophilic Granules | 4 | 4 | 4 | 4 | 4 | 4 | 4 | 4 | 4 |
| Platelets | 4 | 4 | 4 | 4 | 4 | 4 | 4 | 4 | 4 |

TABLE 5-continued

Repeatability data from normal samples stained using accelerated Wright-Giemsa staining procedure.

|  | Day 10 Slide 1 | Day 10 Slide 2 | Day 10 Slide 3 | Day 11 Slide 1 | Day 11 Slide 2 | Day 11 Slide 3 | Day 12 Slide 1 | Day 12 Slide 2 | Day 12 Slide 3 |
|---|---|---|---|---|---|---|---|---|---|
| Erythocytes | 4 | 4 | 4 | 4 | 4 | 4 | 4 | 4 | 4 |
| Eosinophilic Granules | 4 | 4 | 4 | 4 | 4 | 4 | 4 | 4 | 4 |
| Basophilic Granules | 4 | 4 | 4 | N/A | N/A | N/A | N/A | 4 | 4 |
| Leukocyte Nuclei | 4 | 4 | 4 | 4 | 4 | 4 | 4 | 4 | 4 |
| Leukocyte Cytoplasm | 4 | 4 | 4 | 4 | 4 | 4 | 4 | 4 | 4 |
| Nutrophilic Granules | 4 | 4 | 4 | 4 | 4 | 4 | 4 | 4 | 4 |
| Platelets | 4 | 4 | 4 | 4 | 4 | 4 | 4 | 4 | 4 |

|  | Day 13 Slide 1 | Day 13 Slide 2 | Day 13 Slide 3 | Day 14 Slide 1 | Day 14 Slide 2 | Day 14 Slide 3 | Day 15 Slide 1 | Day 15 Slide 2 | Day 15 Slide 3 |
|---|---|---|---|---|---|---|---|---|---|
| Erythocytes | 4 | 4 | 4 | 4 | 4 | 4 | 4 | 4 | 4 |
| Eosinophilic Granules | 4 | 4 | 4 | 4 | 4 | 4 | 4 | 4 | 4 |
| Basophilic Granules | 4 | N/A | N/A | 4 | 4 | 4 | N/A | N/A | N/A |
| Leukocyte Nuclei | 4 | 4 | 4 | 4 | 4 | 4 | 4 | 4 | 4 |
| Leukocyte Cytoplasm | 4 | 4 | 4 | 4 | 4 | 4 | 4 | 4 | 4 |
| Nutrophilic Granules | 4 | 4 | 4 | 4 | 4 | 4 | 4 | 4 | 4 |
| Platelets | 4 | 4 | 4 | 4 | 4 | 4 | 4 | 4 | 4 |

Example 4

Reproducibility of Accelerated Wright-Giemsa Staining Procedure with Abnormal Cells The reproducibility of the accelerated Wright-Giemsa staining procedure described above in Examples 1 and 2 was evaluated by repeatedly performing the staining procedure on 15 separate days. A sample of abnormal cells was stained in triplicate on each day using the accelerated procedure, and the samples were assessed for the staining quality on erythrocytes, eosinophilic granules, basophilic granules, leukocyte nuclei, leukocyte cytoplasm, nutrophilic granules, and platelets using the Stain Quality Scoring Index. The results are summarized below in Table 6.

TABLE 6

Repeatability data from abnormal samples stained using accelerated Wright-Giemsa staining procedure.

| Repeatability Results Abnormal Cells | Day 1 Slide 1 | Day 1 Slide 2 | Day 1 Slide 3 | Day 2 Slide 1 | Day 2 Slide 2 | Day 2 Slide 3 | Day 3 Slide 1 | Day 3 Slide 2 | Day 3 Slide 3 |
|---|---|---|---|---|---|---|---|---|---|
| Erythocytes | 4 | 4 | 4 | 4 | 4 | 4 | 4 | 4 | 4 |
| Eosinophilic Granules | N/A | N/A | N/A | N/A | N/A | N/A | N/A | N/A | N/A |
| Basophilic Granules | 4 | 4 | 4 | N/A | N/A | N/A | N/A | N/A | N/A |
| Leukocyte Nuclei | 4 | 4 | 4 | 4 | 4 | 4 | 4 | 4 | 4 |
| Leukocyte Cytoplasm | 4 | 4 | 4 | 4 | 4 | 4 | 4 | 4 | 4 |
| Nutrophilic Granules | 4 | 4 | 4 | 4 | 4 | 4 | 4 | 4 | 4 |
| Platelets | 4 | 4 | 4 | 4 | 4 | 4 | 4 | 4 | 4 |

|  | Day 4 Slide 1 | Day 4 Slide 2 | Day 4 Slide 3 | Day 5 Slide 1 | Day 5 Slide 2 | Day 5 Slide 3 | Day 6 Slide 1 | Day 6 Slide 2 | Day 6 Slide 3 |
|---|---|---|---|---|---|---|---|---|---|
| Erythocytes | 4 | 4 | 4 | 4 | 4 | 4 | 4 | 4 | 4 |
| Eosinophilic Granules | N/A | 4 | N/A | N/A | N/A | N/A | N/A | N/A | N/A |
| Basophilic Granules | N/A | N/A | 4 | N/A | N/A | N/A | N/A | N/A | N/A |
| Leukocyte Nuclei | 4 | 4 | 4 | 4 | 4 | 4 | 4 | 2 | 4 |
| Leukocyte Cytoplasm | 4 | 4 | 4 | 4 | 4 | 4 | 4 | 2 | 4 |
| Nutrophilic Granules | 4 | 4 | 4 | 4 | 4 | 4 | 4 | 2 | 4 |
| Platelets | 4 | 4 | 4 | 4 | 4 | 4 | 4 | 4 | 4 |

|  | Day 7 Slide 1 | Day 7 Slide 2 | Day 7 Slide 3 | Day 8 Slide 1 | Day 8 Slide 2 | Day 8 Slide 3 | Day 9 Slide 1 | Day 9 Slide 2 | Day 9 Slide 3 |
|---|---|---|---|---|---|---|---|---|---|
| Erythocytes | 4 | 4 | 4 | 4 | 4 | 4 | 4 | 4 | 4 |
| Eosinophilic Granules | 4 | 4 | 4 | 4 | 4 | 4 | 4 | 4 | 4 |
| Basophilic Granules | 4 | 4 | 4 | 4 | 4 | N/A | 4 | N/A | 4 |
| Leukocyte Nuclei | 4 | 4 | 4 | 4 | 4 | 4 | 4 | 4 | 4 |
| Leukocyte Cytoplasm | 4 | 4 | 4 | 4 | 4 | 4 | 4 | 4 | 4 |
| Nutrophilic Granules | 4 | 4 | 4 | 4 | 4 | 4 | 4 | 4 | 4 |
| Platelets | 4 | 4 | 4 | 4 | 4 | 4 | 4 | 4 | 4 |

TABLE 6-continued

Repeatability data from abnormal samples stained using accelerated Wright-Giemsa staining procedure.

| | Day 10 Slide 1 | Day 10 Slide 2 | Day 10 Slide 3 | Day 11 Slide 1 | Day 11 Slide 2 | Day 11 Slide 3 | Day 12 Slide 1 | Day 12 Slide 2 | Day 12 Slide 3 |
|---|---|---|---|---|---|---|---|---|---|
| Erythocytes | 4 | 4 | 4 | 4 | 4 | 4 | 4 | 4 | 4 |
| Eosinophilic Granules | N/A | N/A | N/A | N/A | N/A | N/A | N/A | N/A | N/A |
| Basophilic Granules | N/A | N/A | N/A | N/A | N/A | N/A | N/A | N/A | N/A |
| Leukocyte Nuclei | 4 | 4 | 4 | 4 | 4 | 4 | 4 | 4 | 4 |
| Leukocyte Cytoplasm | 4 | 4 | 4 | 4 | 4 | 4 | 4 | 4 | 4 |
| Nutrophilic Granules | 4 | 4 | 4 | 4 | 4 | 4 | 4 | 4 | 4 |
| Platelets | 4 | 4 | 4 | 4 | 4 | 4 | 4 | 4 | 4 |

| | Day 13 Slide 1 | Day 13 Slide 2 | Day 13 Slide 3 | Day 14 Slide 1 | Day 14 Slide 2 | Day 14 Slide 3 | Day 15 Slide 1 | Day 15 Slide 2 | Day 15 Slide 3 |
|---|---|---|---|---|---|---|---|---|---|
| Erythocytes | 4 | 4 | 3 | 4 | 4 | 4 | 4 | 4 | 4 |
| Eosinophilic Granules | N/A | N/A | N/A | 4 | 4 | 4 | 4 | 4 | 4 |
| Basophilic Granules | N/A | N/A | N/A | 4 | 4 | N/A | N/A | N/A | N/A |
| Leukocyte Nuclei | 4 | 4 | 3 | 4 | 4 | 4 | 4 | 4 | 4 |
| Leukocyte Cytoplasm | 4 | 4 | 3 | 4 | 4 | 4 | 4 | 4 | 4 |
| Nutrophilic Granules | 4 | 4 | 3 | 4 | 4 | 4 | 4 | 4 | 4 |
| Platelets | 4 | 4 | 3 | 4 | 4 | 4 | 4 | 4 | 4 |

Example 5

Acceptability of Accelerated May-Grünwald Staining Procedure with Normal Cells

An accelerated May-Grünwald staining procedure was developed wherein a sample was applied to a substrate and contacted with methanol as a fixation reagent for 30 seconds, followed by contact with a May-Grünwald staining reagent for 180 seconds, followed by contact with phosphate buffer at pH 6.8 for 150 seconds, followed by contact with de-ionized water for 30 seconds, followed by air drying. A sample containing normal cells (i.e., cells with clinically normal morphology) was subjected to this staining procedure and evaluated by 14 different individuals experienced in examining hematology samples. These individuals used the Stain Quality Scoring Index described above to assign numerical scores to the sample in a variety of categories. The numerical scores in each category were then used to create an overall average numerical score for the sample.

In parallel, the same individuals also performed a standard hematology stain on the same sample using their own preferred procedure. The standard staining procedures generally involved longer reagent exposure times for each of the reagents as compared to the accelerated staining procedure described above. The samples that were stained using the standard staining procedure were also evaluated using the Stain Quality Scoring Index and assigned an overall average numerical score.

The results from the analysis of the two samples that underwent different staining procedures were then compared for each of the evaluating individuals. The data are provided in Table 7, below.

TABLE 7

Comparison of numerical score assigned to normal cells stained with standard staining procedure and accelerated May-Grünwald staining procedure.

| | Individual | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Standard Staining Procedure | 3.8 | 3.3 | 3.9 | n/a | 3.9 | 3.3 | 3.8 | 2.0 | 3.9 | 3.6 | 4.0 | 2.7 | 2.6 | 3.7 |
| Accelerated May-Grünwald Staining Procedure | 3.1 | 3.4 | 3.4 | 3.9 | 3.5 | 3.9 | 3.1 | 2.6 | 4.0 | 3.2 | 3.7 | 3.8 | 3.0 | 3.7 |

Example 6

Acceptability of Accelerated May-Grünwald Staining Procedure with Abnormal Cells An accelerated May-Grünwald staining procedure was developed wherein a sample was applied to a substrate and contacted with methanol as a fixation reagent for 30 seconds, followed by contact with a May-Grünwald staining reagent for 180 seconds, followed by contact with phosphate buffer at pH 6.8 for 150 seconds, followed by contact with de-ionized water for 30 seconds, followed by air drying. A sample containing abnormal cells (i.e., cells with clinically abnormal morphology) was subjected to this staining procedure and evaluated by 14 different individuals experienced in examining hematology samples. These individuals used the Stain Quality Scoring Index described above to assign numerical scores to the sample in a variety of categories. The numerical scores in each category were then used to create an overall average numerical score for the sample.

In parallel, the same individuals also performed a standard hematology stain on the same sample using their own preferred procedure. The standard staining procedures generally involved longer reagent exposure times for each of the reagents as compared to the accelerated staining procedure described above. The samples that were stained using the standard staining procedure were also evaluated using the Stain Quality Scoring Index and assigned an overall average numerical score.

The results from the analysis of the two samples that underwent different staining procedures were then compared for each of the evaluating individuals. The data are provided in Table 8, below.

TABLE 8

Comparison of numerical score assigned to abnormal cells stained with standard staining procedure and accelerated May-Grünwald staining procedure.

| | Individual | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Standard May-Grünwald Staining Procedure | 2.0 | 3.3 | 3.4 | n/a | 2.1 | 3.1 | 2.9 | 2.0 | 2.8 | 3.6 | 3.8 | 2.4 | 2.9 | 3.0 |
| Accelerated May-Grünwald Staining Procedure | 2.3 | 2.2 | 2.1 | 3.9 | 2.4 | 3.7 | 2.6 | 2.6 | 3.0 | 2.9 | 2.3 | 2.4 | 2.6 | 2.3 |

Example 7

Accelerated May-Grünwald Staining Procedure Using De-Ionized Water and No Phosphate Buffer An accelerated May-Grünwald staining procedure was developed wherein a sample was applied to a microscope slide, contacted with methanol as a fixation reagent for 30 seconds and contacted with a May-Grünwald staining reagent for 180 seconds. Following contact with the May-Grünwald staining reagent, the slide was evenly coated with de-ionized water without draining the May-Grünwald staining reagent, and the slide was then allowed to sit for 90 seconds. Next, the slide was rinsed for 10 seconds in de-ionized water. The slide was then dried and examined. Microscopic examination revealed that the sample has been successfully stained.

Incorporation by Reference

This application is related to co-pending and co-owned provisional applications: AUTOMATED SMEAR MAKING APPARATUS (U.S. Provisional Patent Application Ser. No. 61/581,032) and MICROSCOPE SLIDE CARRIER (U.S. Provisional Patent Application Ser. No. 61/581,037), the disclosures of which are herein incorporated by reference in their entirety.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An automated staining system for performing a Wright-Giemsa stain on one or more samples, comprising:
    a sample application subsystem that applies a sample to a substrate;
    a fixation reagent bath;
    a Wright-Giemsa staining reagent bath;
    a rinse reagent bath;
    a sample transfer subsystem for moving the substrate from the sample application subsystem, to the fixation reagent bath, to the Wright-Giemsa staining bath, and then to the rinse reagent bath; and
    a computer readable storage medium comprising instructions executable by at least one processing device that, when executed, cause the processing device to control the sample transfer subsystem such that the sample transfer subsystem places the one or more samples
    in the fixation reagent bath for a period of time ranging from about 15 seconds up to about 45 seconds,
    in the Wright-Giemsa staining reagent bath for a period of time ranging from about 15 seconds up to about 60 seconds, and
    in the rinse reagent bath for a period of time ranging from about 105 seconds up to about 135 seconds,
    wherein the substrate remains motionless for the period of time during which the sample is contacted with each reagent.

2. The system of claim 1, wherein the sample is placed in the fixation reagent bath for a period of time ranging from about 20 seconds up to about 40 seconds.

3. The system of claim 1, wherein the sample is placed in the fixation reagent bath for a period of time ranging from about 25 seconds up to about 35 seconds.

4. The system of claim 1, wherein the fixation reagent is methanol.

5. The system of claim 1, wherein the sample is placed in the Wright-Giemsa staining reagent bath for a period of time ranging from about 20 seconds up to about 50 seconds.

6. The system of claim 1, wherein the sample is placed in the Wright-Giemsa staining reagent bath for a period of time ranging from about 25 seconds up to about 45 seconds.

7. The system of claim 1, wherein the Wright-Giemsa staining reagent comprises methanol.

8. The system of claim 1, wherein the sample is placed in the rinse reagent bath for a period of time ranging from about 110 seconds up to about 130 seconds.

9. The system of claim 1, wherein the sample is placed in the rinse reagent bath for a period of time ranging from about 115 seconds up to about 125 seconds.

10. The system of claim 1, wherein the rinse reagent comprises de-ionized water.

11. The system of claim 1, wherein the rinse reagent is a phosphate buffer.

12. The system of claim 11, wherein the phosphate buffer is a high salt phosphate buffer.

13. The system of claim 11, wherein the phosphate buffer is a low salt phosphate buffer.

14. The system of claim 11, wherein the phosphate buffer has a pH value ranging from about 5.0 up to about 9.0 pH units.

15. The system of claim 11, wherein the phosphate buffer has a pH value ranging from about 6.5 up to about 7.0 pH units.

16. The system of claim 1, further comprising placing the sample in a second rinse reagent bath for a period of time ranging from about 5 seconds up to about 30 seconds.

17. The system of claim 16, wherein the sample is placed in the second rinse reagent bath for a period of time ranging from about 10 seconds up to about 25 seconds.

18. The system of claim 16, wherein the sample is placed in the second rinse reagent bath for a period of time ranging from about 10 seconds up to about 20 seconds.

19. The system of claim 16, wherein the second rinse reagent comprises de-ionized water.

20. The system of claim 16, wherein the second rinse reagent is a phosphate buffer.

21. The system of claim 20, wherein the phosphate buffer is a high salt phosphate buffer.

22. The system of claim 20, wherein the phosphate buffer is a low salt phosphate buffer.

23. The system of claim 20, wherein the phosphate buffer has a pH value ranging from about 5.0 up to about 9.0 pH units.

24. The system of claim 20, wherein the phosphate buffer has a pH value ranging from about 6.5 up to about 7.0 pH units.

25. The system of claim 1, further comprising placing the sample in a drying chamber.

26. The system of claim 1, wherein the substrate is a glass microscope slide.

27. The system of claim 1, wherein the sample is a biological fluid.

28. The system of claim 1, wherein the sample is a blood sample.

29. The system of claim 1, wherein the sample is a bone marrow sample.

30. The automated staining system according to claim 1, wherein the concentration of each reagent remains constant during the period of time that the sample is contacted with the reagent.

31. An automated staining system for performing a May-Grünwald stain on one or more samples, comprising:
a sample application subsystem that applies a sample to a substrate;
a fixation reagent bath;
a May-Grünwald staining reagent bath;
a rinse reagent bath;
a sample transfer subsystem for moving the substrate from the sample application subsystem, to the fixation reagent bath, to the May-Grünwald staining bath, and then to the rinse reagent bath; and
a computer readable storage medium comprising instructions executable by at least one processing device that, when executed, cause the processing device to control the sample transfer subsystem such that the sample transfer subsystem places the one or more samples in the fixation reagent bath for a period of time ranging from about 15 seconds up to about 45 seconds,
in the May-Grünwald staining reagent bath for a period of time ranging from about 165 seconds up to about 195 seconds, and
in the rinse reagent bath for a period of time ranging from about 135 seconds up to about 165 seconds,
wherein the substrate remains motionless for the period of time during which the sample is contacted with each reagent.

32. The system of claim 31, wherein the sample is placed in the fixation reagent bath for a period of time ranging from about 20 seconds up to about 40 seconds.

33. The system of claim 31, wherein the sample is placed in the fixation reagent bath for a period of time ranging from about 25 seconds up to about 35 seconds.

34. The system of claim 31, wherein the fixation reagent is methanol.

35. The system of claim 31, wherein the sample is placed in the May-Grünwald staining reagent bath for a period of time ranging from about 170 seconds up to about 190 seconds.

36. The system of claim 31, wherein the sample is placed in the May-Grünwald staining reagent bath for a period of time ranging from about 175 seconds up to about 185 seconds.

37. The system of claim 31, wherein the May-Grünwald staining reagent comprises methanol.

38. The system of claim 31, wherein the sample is placed in the rinse reagent bath for a period of time ranging from about 140 seconds up to about 160 seconds.

39. The system of claim 31, wherein the sample is placed in the rinse reagent bath for a period of time ranging from about 145 seconds up to about 155 seconds.

40. The system of claim 31, wherein the rinse reagent comprises de-ionized water.

41. The system of claim 31, wherein the rinse reagent is a phosphate buffer.

42. The system of claim 41, wherein the phosphate buffer is a high salt phosphate buffer.

43. The system of claim 41, wherein the phosphate buffer is a low salt phosphate buffer.

44. The system of claim 41, wherein the phosphate buffer has a pH value ranging from about 5.0 up to about 9.0 pH units.

45. The system of claim 41, wherein the phosphate buffer has a pH value ranging from about 6.5 up to about 7.0 pH units.

46. The system of claim 31, further comprising placing the sample in a second rinse reagent bath for a period of time ranging from about 15 seconds up to about 45 seconds.

47. The system of claim 46, wherein the sample is placed in the second rinse reagent bath for a period of time ranging from about 20 seconds up to about 40 seconds.

48. The system of claim 46, wherein the sample is placed in the second rinse reagent bath for a period of time ranging from about 25 seconds up to about 35 seconds.

49. The system of claim 46, wherein the second rinse reagent comprises de-ionized water.

50. The system of claim 46, wherein the second rinse reagent is a phosphate buffer.

51. The system of claim 50, wherein the phosphate buffer is a high salt phosphate buffer.

52. The system of claim 50, wherein the phosphate buffer is a low salt phosphate buffer.

53. The system of claim 50, wherein the phosphate buffer has a pH value ranging from about 5.0 up to about 9.0 pH units.

54. The system of claim 50, wherein the phosphate buffer has a pH value ranging from about 6.5 up to about 7.0 pH units.

55. The system of claim 31, further comprising placing the sample in a drying chamber.

56. The system of claim 31, wherein the substrate is a glass microscope slide.

57. The system of claim 31, wherein the sample is a biological fluid.

58. The system of claim 31, wherein the sample is a blood sample.

59. The system of claim 31, wherein the sample is a bone marrow sample.

60. The automated staining system according to claim 31, wherein the concentration of each reagent remains constant during the period of time that the sample is contacted with the reagent.

\* \* \* \* \*